US006046359A

United States Patent [19]

Wulff-Döring et al.

[11] Patent Number: 6,046,359

[45] Date of Patent: Apr. 4, 2000

[54] CATALYSTS FOR THE AMINATION OF ALKYLENE OXIDES, ALCOHOLS, ALDEHYDES AND KETONES

[75] Inventors: Joachim Wulff-Döring, Frankenthal; Johann-Peter Melder, Neuhofen; Gerhard Schulz, Ludwigshafen; Guido Voit, Schriesheim, all of Germany; Gutshoven Frank, Gent, Belgium; Wolfgang Harder, Weinheim, Germany

[73] Assignee: BASF Aktiengesellschaft, Ludwigshafen, Germany

[21] Appl. No.: 09/262,262

[22] Filed: Mar. 4, 1999

Related U.S. Application Data

[62] Division of application No. 08/955,264, Oct. 21, 1997, Pat. No. 5,916,838.

[30] Foreign Application Priority Data

Oct. 31, 1996 [DE] Germany ........................... 196 44 107

[51] Int. Cl.[7] .................................................. C07C 209/00

[52] U.S. Cl. .......................... 564/398; 564/305; 564/395; 564/399; 564/401

[58] Field of Search .................................... 564/305, 395, 564/398, 399, 401

[56] References Cited

FOREIGN PATENT DOCUMENTS

| 146508 | 6/1985 | European Pat. Off. . |
|---|---|---|
| 254335 | 1/1988 | European Pat. Off. . |
| 312253 | 1/1989 | European Pat. Off. . |

*Primary Examiner*—Paul J. Killos
*Attorney, Agent, or Firm*—Keil & Weinkauf

[57] ABSTRACT

A catalyst comprises, based on the total weight of the catalyst, 0.1–6% by weight of cobalt, nickel or a mixture thereof, 0.001–25% by weight of ruthenium, 0–10% by weight of copper and 0–5% by weight of promoters on a porous metal oxide carrier.

It preferably comprises 0.1–3% by weight of cobalt and 0.1–3% by weight of nickel. It can be used in hydrogenation reactions, dehydrogenation reactions or hydrogenation/dehydrogenation reactions, in particular in the amination of alkylene oxides, alcohols, aldehydes or ketones with ammonia or primary or secondary amines.

3 Claims, No Drawings

CATALYSTS FOR THE AMINATION OF ALKYLENE OXIDES, ALCOHOLS, ALDEHYDES AND KETONES

This application is a divisional of application Ser. No. 08/955,264 filed Oct. 21, 1997, now U.S. Pat. No. 5,916, 838.

BACKGROUND OF THE INVENTION

1. Field of the Invention

The present invention relates to ruthenium-, nickel- and/ or cobalt-containing catalysts which can be used for aminating alkylene oxides, alcohols, aldehydes and ketones. The present invention furthermore relates to processes for the preparation of the catalysts, the use thereof in amination reactions and processes for the preparation of amination products.

2. Description of Related Art

EP-A-0 146 508 discloses dehydrogenation/ hydrogenation catalysts which contain ruthenium, nickel and/or cobalt. The catalysts used contain about 0.25–1.0% by weight of ruthenium and 7.5 or 10% by weight of nickel or 10% by weight of cobalt or 4% by weight of nickel and 4% by weight of cobalt, based on the total weight of the catalyst, on an alumina carrier. In addition to nickel, the catalysts may also contain copper and chromium in addition to nickel, and also iron in addition to nickel and cobalt. The ruthenium is applied to the catalyst in the form of a solution of a ruthenium halide. The catalyst is used, for example, for aminating monoethanolamine with ammonia, the reaction being carried out in an autoclave.

EP-A-0 254 335 discloses a process for the preparation of a hydrogenation and/or dehydrogenation catalyst, about 10% by weight of nickel or cobalt and about 0.5% by weight of ruthenium, based on the total weight of the catalyst, being applied to an alumina carrier. The catalyst is prepared by impregnating the carrier with a nickel nitrate or cobalt nitrate solution, then impregnating with aqueous hydrochloric acid and subsequently impregnating with a solution of ruthenium nitrosyl nitrate. A ruthenium halide is not used for coating the carrier. The catalyst is used for reacting monoethanolamine with ammonia in an autoclave.

The known catalysts have high contents of nickel and/or cobalt. Furthermore, the stability is insufficient, particularly in the case of the catalysts described in EP-A-0 254 335. The selectivities with respect to ethylenediamine which are obtained in the reaction of monoethanolamine with ammonia are insufficient in the continuous procedure.

SUMMARY OF THE INVENTION

It is an object of the present invention to provide amination catalysts which avoid the disadvantages of the known catalysts and in particular have a low content of nickel and/or cobalt in combination with good stability and high selectivity with respect to ethylenediarnine in the amination of monoethanolamine with ammonia.

DETAILED DESCRIPTION OF THE INVENTION

We have found that this object is achieved by providing a catalyst comprising, based on the total weight of the catalyst, 0.1–6% by weight of cobalt, nickel or a mixture thereof, 0.001–25% by weight of ruthenium, 0–10% by weight of copper and 0–5% by weight of promoters selected from the group consisting of iron, rhodium, palladium, platinum, iridium, osmium, silver, gold, chromium, molybdenum, tungsten, rhenium, zinc, cadmium, lead, manganese, tin, lithium, sodium, potassium, rubidium, cesium, phosphorus, arsenic, antimony, bismuth, tellurium, thallium or mixtures thereof on a porous metal oxide carrier.

The catalyst carrier used is a porous metal oxide which is selected from the group consisting of alumina, aluminosilicates, titanium dioxide, zirconium dioxide, magnesium oxide and mixtures thereof. Carriers which contain alumina are preferably used, particularly preferably those consisting of alumina.

0.1–6, preferably 0.2–4, in particular 0.4–2, % by weight of cobalt, nickel or a mixture thereof are applied to the catalyst carrier. The stated weights are based on the total weight of the catalyst unless stated otherwise. Preferably 0.1–3, particularly preferably 0.2–2, in particular 0.4–1, % by weight of cobalt are applied. Likewise, preferably 0.1–3, particularly preferably 0.2–2, in particular 0.4–1, % by weight of nickel are applied.

The catalyst furthermore contains 0.001–25, often 0.01–25, preferably 0.1–10, particularly preferably 0.3–4, in particular 0.5–2.5, % by weight of ruthenium on the carrier.

In addition, copper may be applied to the carrier. The copper content is 0–10% preferably 0.1–7, particularly preferably 0.5–4, % by weight.

0–5% by weight of promoters may also be present on the carrier. They are selected from the group consisting of iron, rhodium, palladium, platinum, iridium, osmium, silver, gold, chromium, molybdenum, tungsten, rhenium, zinc, cadmium, lead, manganese, tin, lithium, sodium, potassium, rubidium, cesium, phosphorus, arsenic, antimony, bismuth, tellurium, thallium and mixtures thereof.

The catalyst particularly preferably contains 0.4–1% by weight of cobalt, 0.4–1% by weight of nickel, 0.3–4% by weight of ruthenium and 0.5–4% by weight of copper. In particular, the nickel content is 0.7–0.9% by weight, the cobalt content 0.7–0.9% by weight, the copper content 1.3–1.9% by weight and the ruthenium content 0.5–2.5% by weight.

By additionally doping the catalyst carriers with the abovementioned promoters, the selectivity of the catalyst can be controlled. The promoter content is preferably 0.001–5, in particular 0.01–3, % by weight.

The catalysts are prepared by (a) coating the carrier with the metals, promoters or compounds thereof, (b) drying and calcining the impregnated carrier and (c) reducing the calcined carrier in a stream of hydrogen.

Below, the metals and the promoters are discussed and are referred to together as metals.

The carrier can be coated with the metals or compounds of the metals in step (a) by any desired suitable method. For example, the carrier may be impregnated with a solution of the metal compounds. Impregnation of the carrier may also be effected by spraying on the solutions or kneading the carrier together with the solutions or by precipitating the metals or metal compounds onto the carrier.

The metals with which the carrier is impregnated are preferably used in the form of a solution of the salts of the metals. For example, the nitrates, halides, in particular chlorides, formates, oxalates or amrnoniates, preferably the oxalates and nitrates, particularly preferably the nitrates, may be used. In one embodiment of the invention, ruthenium is used in the form of a halide-containing solution. The solution can be prepared from the halides of ruthenium, in particular from chlorides. Preferably, ruthenium is used in the form of a halide-free solution, particularly preferably in the form of a solution of a salt as described above. Oxalates and nitrates are particularly preferred, in particular nitrates of ruthenium.

In a particularly preferred embodiment of the invention, the carrier is not impregnated with halide compounds. In particular, the carrier is not impregnated with metal halides or solutions of the metal halides or with another halide-containing solution, such as aqueous hydrochloric acid solution.

The present invention also relates to a catalyst as described above, which can be prepared by (a) impregnating the carrier with the metals, promoters or compounds thereof, (b) drying and calcining the impregnated carrier and (c) reducing the calcined carrier in a stream of hydrogen, the carrier not being impregnated with halogen compounds.

In particular, impregnation of the carrier with an aqueous hydrochloric acid solution, as described in EP-A1-0 254 335, can lead to poorer mechanical properties of the catalyst since the oxidic carriers may be attacked by the acid The mechanical stability of the catalyst may be reduced as a result so that the life of the catalyst decreases during operation owing to catalyst disintegration. Both in the catalyst preparation and in reactions with the catalyst, chlorides present on the catalyst carrier may furthermore lead to corrosion problems if, for example, hydrochloric acid is liberated from the catalyst. The catalyst is therefore preferably halogen-free and no halides, in particular chlorides, are used in the preparation of the catalyst. In particular, the catalyst carrier is preferably not impregnated with halogen compounds.

The impregnation of the catalyst with the metals or metal salt solutions can be carried out in any desired order. For example, the catalyst carrier can be impregnated with a solution which contains all metal salts. The carrier may also be impregnated in succession with a plurality of solutions which contain the salts of one or more of the metals used. All or individual impregnation steps may be applied several times, it being possible to change the order of the impregnations. In the case of multiple impregnations, in particular when the solutions are sprayed on several times or the carrier impregnated several times with the solutions, the concentrations of the metal salts in the solutions may be kept low.

The concentration in the solutions or solution can also be established so that the desired amount of metal is present on the carrier as a result of a single application or impregnation. After the impregnation of the carrier with the metals or compounds of the metals, the impregnated carrier is preferably dried at 80–150° C., particularly preferably 80–120° C. The impregnated carrier is then calcined at 150–500° C., preferably 300–500° C. The impregnated and calcined carrier is then reduced in a stream of hydrogen at 150–500° C., preferably 200–400° C. For this purpose, the carrier is preferably first cooled after the calcination. The stream of hydrogen may be used as a pure hydrogen stream or as a dilute hydrogen stream, for example in an inert gas, such as nitrogen.

The reduction, which may also be referred to as activation, can be carried out directly in the reactor which is also used for the subsequent synthesis. If the reduction of the catalysts is carried out in a separate reactor, the catalysts are superficially passivated before being removed from the reactor, preferably at 10–60° C., in particular 20–40° C., with a gas mixture which contains free oxygen. After installation in the reactor intended for the synthesis, the catalysts passivated in this manner may be activated in a stream of hydrogen, preferably a nitrogen/hydrogen stream, at 150–200° C., preferably 170–190° C. They can also be used without further activation.

The novel catalysts can be used in any suitable form, for example as moldings, such as extrudates or pellets, or in powder form. Shaped carriers may be impregnated with the metals or metal compounds, or impregnated carriers may be brought to the desired shape. When carrier and metals or metal compounds are kneaded together or precipitated together, the resulting materials are as a rule subsequently molded. Particularly in the continuous procedure, the catalysts are used in the form of moldings.

The novel catalysts can be used in a large number of reactions. According to the invention, they are preferably used in hydrogenation reactions, dehydrogenation reactions or hydrogenation/dehydrogenation reactions. In particular, the catalysts are used for aminating alkylene oxides, alcohols, aldehydes or ketones with ammonia or primary or secondary amines. Particularly preferably, the catalysts are used for aminating alcohols, especially in the reaction of monoethanolamine with ammonia to give ethylenediamine. The novel catalysts are mechanically stable over a long time and show no decrease in activity. In combination with the same activity as the known catalysts having a high content of nickel and cobalt, they exhibit higher activity with regard to the formation of primary amination products in the amination with ammonia. They also have a substantially improved life. Owing to the low content of nickel and cobalt, they can be prepared more economically.

The present invention also relates to a process for the preparation of amination products by reacting alkylene oxides, alcohols, aldehydes and ketones with ammonia or primary or secondary amines in the presence of free hydrogen and in the presence of a catalyst as described above.

The amination is carried out by reacting ammonia or a primary or secondary amino group with a hydroxyl group, an aldehyde or keto group or an alkylene oxide group, aldehyde, keto or alkylene oxide groups undergoing reductive amination or hydroxyl groups being replaced by amino groups. The amino groups or groups to be aminated may be present in different molecules or in the same molecule. If the groups to be reacted with one another are present in the same molecule, cyclic compounds may result. The compounds in which amino groups and groups to be aminated are present may furthermore act either as an amine component or as a compound to be aminated.

For example, inter alia, ethylenediamine (EDA), aminoethylethanolamine (AEEA), diethylenetriamine (DETA) and piperazine may be obtained in the amination of monoethanolamine (MEA) with ammonia.

It is also possible to use compounds which have two or more of the hydroxyl, aldehyde, keto or alkylene oxide groups. Mixed groups may also be present. In particular, diols or polyols may be used, especially ethylene glycols. Other suitable compounds are those which have a plurality of primary or secondary amino groups, such as alkylenediamines, in particular ethylenediamine. For example, ethylene glycols or ethanolamines can be aminated with, or in the presence of, ammonia, ethanolamines, ethylenediamines or diethylenetriamines.

In one embodiment of the invention, the novel process is used for the preparation of amines of the general formula (I)

$$R^1R^2N—CHR^3R^4 \qquad (I)$$

where $R^1$, $R^2$, $R^3$ and $R^4$ independently are each hydrogen, $C_1$–$C_{200}$-alkyl, $C_3$–$C_{12}$-cycloalkyl, amino-, $C_1$–$C_{20}$-alkylamino-, di-$C_1$–$C_{20}$-alkylamino- and/or hydroxyl-substituted $C_1$–$C_{20}$-alkyl, $C_2$–$C_{30}$-alkoxyalkyl, $R^5(OCHR^6CH_2)_n$, aryl, $C_7$–$C_{20}$-aralkyl or $C_7$–$C_{20}$-alkylaryl, or $R^1$ and $R^2$ together form $(CH_2)_1$—X—$(CH_2)_m$, where $R^5$ is hydrogen or $C_1$–$C_4$-alkyl, $R^6$ is hydrogen or methyl, X is oxygen or $NR^6$, n is an integer from 2 to 30, 1 is an integer from 2 to 4 and m is an integer from 1 to 4, from primary or secondary alcohols, ketones, aldehydes of the general formula (II)

$$R^3R^4CHOH \text{ or } R^3R^4CO \quad \text{(II)}$$

where $R^3$ and $R^4$ have the abovementioned meanings, and primary or secondary amines of the general formula (III)

$$R^1R^2NH \quad \text{(III)}$$

where $R^1$ and $R^2$ have the abovementioned meanings.

$R^1$, $R^2$, $R^3$ and $R^4$, in particular $R^1$ and $R^2$, may be $C_1$–$C_{200}$-alkyl, preferably $C_1$–$C_8$-alkyl, such as methyl, ethyl, n-propyl, isopropyl, n-butyl, isobutyl, sec-butyl, tert-butyl, n-pentyl, isopentyl, sec-pentyl, neopentyl, 1,2-dimethylpropyl, n-hexyl, isohexyl, sec-hexyl, n-heptyl, isoheptyl, n-octyl, isooctyl, 2-ethylhexyl, n-decyl, 2-n-propyl-n-heptyl, n-tridecyl, 2-n-butyl-n-nonyl or 3-n-butyl-n-nonyl, particularly preferably isopropyl, 2-ethylhexyl, n-decyl, 2-n-propyl-n-heptyl, n-tridecyl, 2-n-butyl-n-nonyl or 3-n-butyl-n-nonyl, or $C_{40}$–$C_{200}$-alkyl, such as polybutyl, polyisobutyl, polypropyl, polyisopropyl or polyethyl, particularly preferably polybutyl or polyisobutyl.

$R^1$ and $R^2$ together may be —$(CH_2)_1$—X—$(CH_2)_m$, where X is oxygen or N—$R^6$ having the meanings stated below and 1 is an integer from 2 to 4, such as 2, 3 or 4, preferably 2 or 3, particularly preferably 2, and m is an integer from 1 to 4, such as 1, 2, 3 or 4, preferably 2, 3 or 4, particularly preferably 2 or 3.

$R^1$, $R^2$, $R^3$ and $R^4$ may each be $C_3$–$C_{12}$-cycloalkyl, preferably $C_3$–$C_8$-cycloalkyl, such as cyclopropyl, cyclobutyl, cyclopentyl, cyclohexyl, cycloheptyl or cyclooctyl, particularly preferably cyclopentyl, cyclohexyl or cyclooctyl.

They may be aryl, such as phenyl, 1-naphthyl, 2-naphthyl, 1-anthryl, 2-anthryl or 9-anthryl, preferably phenyl, 1-naphthyl or 2-naphthyl, particularly preferably phenyl.

They may be $C_7$–$C_{20}$-alkylaryl, preferably $C_7$–$C_{12}$-alkylphenyl, such as 2-methylphenyl, 3-methylphenyl, 4-methylphenyl, 2,4-dimethylphenyl, 2,5-dimethylphenyl, 2,6-dimethylphenyl, 3,4-dimethylphenyl, 3,5-dimethylphenyl, 2,3,4-trimethylphenyl, 2,3,5-trimethylphenyl, 2,3,6-trimethylphenyl, 2,4,6-trimethylphenyl, 2-ethylphenyl, 3-ethylphenyl, 4-ethylphenyl, 2-n-propylphenyl, 3-n-propylphenyl or 4-n-propylphenyl.

They may be $C_7$–$C_{20}$-aralkyl, preferably $C_7$–$C_{12}$-phenylalkyl, such as benzyl, 1-phenylethyl, 2-phenylethyl, 1-phenylpropyl, 2-phenylpropyl, 3-phenylpropyl, 1-phenylbutyl, 2-phenylbutyl, 3-phenylbutyl or 4-phenylbutyl, particularly preferably benzyl, 1-phenylethyl or 2-phenylethyl.

$R^1$ may be in particular $C_1$–$C_{20}$-alkyl, preferably $C_1$–$C_8$-alkyl, such as methyl, ethyl, n-propyl, isopropyl, n-butyl, isobutyl, 6-butyl, tert-butyl, n-pentyl, isopentyl, sec-pentyl, neopentyl, 1,2-dimethylpropyl, n-hexyl, isohexyl, sechexyl, n-heptyl, isoheptyl, n-octyl, isooctyl, particularly preferably $C_1$–$C_4$-alkyl, such as methyl, ethyl, n-propyl, isopropyl, n-butyl, isobutyl, sec-butyl or tert-butyl.

$R^3$ and $R^4$ may be in particular $C_1$–$C_{20}$-hydroxyalkyl, preferably $C_1$–$C_8$-hydroxyalkyl, particularly preferably $C_1$–$C_4$-hydroxyalkyl, such as hydroxymethyl, 1-hydroxyethyl, 2-hydroxyethyl, 1-hydroxy-n-propyl, 2-hydroxyl-n-propyl, 3-hydroxy-n-propyl or 1-hydroxymethylethyl, or amino- and/or alkylamino- and/or dialkylamino- and/or hydroxyl-substituted $C_1$–$C_{20}$-alkyl, preferably $C_1$–$C_8$-alkyl, particularly preferably $C_1$–$C_4$-alkyl, such as n-(hydroxyethyl)aminoethyl or N-(aminoethyl)aminoethyl.

They may be $C_2$–$C_{30}$-alkoxyalkyl, preferably $C_2$–$C_{20}$-alkoxyalkyl, particularly preferably $C_2$–$C_8$-alkoxyalkyl, such as methoxymethyl, ethoxymethyl, n-propoxymethyl, isopropoxymethyl, n-butoxymethyl, isobutoxymethyl, sec-butoxymethyl, tert-butoxymethyl, 1-methoxymethyl or 2-methoxymethyl, particularly preferably $C_2$–$C_4$-alkoxyalkyl, such as methoxymethyl, ethoxymethyl, n-propoxymethyl, isopropoxymethyl, n-butoxymethyl, isobutoxymethyl, sec-butoxymethyl, tert-butoxymethyl, 1-methoxyethyl or 2-methoxyethyl.

They may be $R^5$—$(OCHR^6CH_2)_n$, where $R^5$ is $C_1$–$C_4$-alkyl, such as methyl, ethyl, n-propyl, isopropyl, n-butyl, isobutyl, sec-butyl or tert-butyl, preferably methyl or ethyl, particularly preferably methyl. $R^6$ is hydrogen or methyl.

n is an integer from 2 to 10, preferably from 2 to 8, such as 2, 3, 4, 5, 6, 7 or 8, particularly preferably 2, 3, 4, 5 or 6.

All radicals $R^1$ to $R^6$ may furthermore be hydrogen.

The novel process can be carried out batchwise or, preferably, continuously. The continuous procedure is preferably carried out in a tubular reactor by the trickle-bed or liquid phase method. Particularly in the amination of alcohols, temperatures of 120–250° C., preferably 150–190° C., and pressures of 150–300, preferably 180–220, bar are employed. In general, temperatures of 80–250° C. and pressures of 100–400 bar can be employed.

In the reaction with ammonia, ammonia may be used as a reagent or as a solvent. 1–20, preferably 6–12, mol of ammonia may be used per mol of alkylene oxide, alcohol, aldehyde or ketone. The catalyst space velocity is preferably from 0.05 to 2.0, particularly preferably from 0.1 to 1.0, kg of alkylene oxide, alcohol, aldehyde or ketone per liter of catalyst per hour. The reaction may also be carried out in the presence of water, it being possible to add up to 15% by weight, based on the total reaction mixture, of water.

The use of the novel catalysts in the process according to the invention permits, in particular in the reaction of monoethanolamine with ammonia, a high yield of ethylenediamine owing to the high selectivity of the novel catalysts.

The products obtained by the novel process are suitable, inter alia, as intermediates for the preparation of fuel additives, for example described in U.S. Pat. No. 3,275,554, DE-A-21 25 039 or DE-A-36 11 230. The compounds obtained according to the invention can also be used in the preparation of surfactants, drugs and crop protection agents as well as vulcanization accelerators. The Examples which follow illustrate the invention.

EXAMPLE 1

135 g of $Al_2O_3$ extrudates having a diameter of 4 mm (D10-10, produced by BASF AG, Ludwigshafen) were left to stand with 88 ml of an aqueous impregnating solution which contained 1.4 g of NiO, 1.4 g of CoO and 2.5 g of CuO, with repeated thorough mixing at room temperature for two hours. The catalyst precursor was dried for 16 hours at 120° C. and calcined for four hours at 400° C. The extrudates were then impregnated with 88 ml of an aqueous ruthenium chloride solution which contained 1.41 g of ruthenium. Nickel, cobalt and copper were used in the form of nitrates.

The catalyst precursor was then dried for 16 hours at 120° C. and for four hours at 400° C. After cooling, the extrudates were installed in a reduction apparatus and flushed for two hours with 20 l of $N_2$ per hour. Heating was then carried out to 300° C. at a rate of 2° C./min and with a hydrogen flow rate of 20 l of $H_2$ per hour, and this temperature was maintained for 20 hours. After cooling in a stream of nitrogen, the catalyst was passivated with an air/nitrogen mixture, a maximum temperature increase of 20° C. being permitted. The catalyst thus prepared contained 1% by weight of ruthenium, 0.79% by weight of nickel, 0.79% by weight of cobalt and 1.6% by weight of copper on alumina. The results in the amination of monoethanolamine are listed in Table 1. The catalyst was still completely intact after an operating time of 143 hours.

EXAMPLE 2

The catalyst was prepared similarly to Example 1. The results in the amination of monoethanolamine with a reduced conversion compared with Example 1 are listed in Table 1. The catalyst was completely intact after an operating time of 133 hours.

EXAMPLE 3

The catalyst was prepared similarly to Example 1. The results in the amination of monoethanolamine with a reduced conversion compared with Example 1 are listed in Table 1. The catalyst was still completely intact after an operating time of 153 hours.

EXAMPLE 4

The catalyst was prepared similarly to Example 1, except that 500 g of the $Al_2O_3$ extrudates were impregnated with 311 ml of an aqueous impregnating solution which contained 5.3 g of NiO, 5.3 g of CoO and 10.6 g of CuO in the form of the nitrates and were then dried and calcined. The extrudates were then impregnated with 248 ml of an aqueous ruthenium nitrate solution which contained 10.6 g of ruthenium. Drying and calcination as well as reduction were carried out as stated in Example 1. The catalyst thus prepared contained 2% by weight of ruthenium, 0.79% by weight of nickel, 0.79% by weight of cobalt and 1.6% by weight of copper on alumina. The results in the amination of monoethanolamine are listed in Table 1. The catalyst was still completely intact after an operating time of 141 hours.

The conversion was varied in Examples 5 to 7 below.

EXAMPLE 5

The catalyst was prepared similarly to Example 4. The results in the amination of monoethanolarnine are listed in Table 1. The catalyst was still completely intact after an operating time of 283 hours.

EXAMPLE 6

The catalyst was prepared similarly to Example 4. The results in the amination of monoethanolamine are listed in Table 1. The catalyst was still completely intact after an operating time of 141 hours.

EXAMPLE 7

The catalyst was prepared similarly to Example 4. The results in the animation of monoethanolamine are listed in Table 1. The catalyst was still completely intact after an operating time of 251 hours.

COMPARATIVE EXAMPLE V1

The catalyst was prepared by the process stated in EP-A1-0 254 335, Example 1. The catalyst thus obtained contained 10% by weight of nickel and 0.5% by weight of ruthenium on alumina (D10-10 from BASF AG, Ludwigshafen). The results in the amination of monoethanolamine are listed in Table 1. The catalyst had completely disintegrated after an operating time of 48 hours.

COMPARATIVE EXAMPLE V2

The catalyst was prepared by the process stated in EP-A1-0 254 335, Example 13. The catalyst thus obtained contained 10% by weight of cobalt and 0.5% by weight of ruthenium on alumina (D10-10 from BASF AG, Ludwigshafen). The results in the amination of monoethanolamine are listed in Table 1. The catalyst had completely disintegrated after an operating time of 48 hours.

Amination:

The amination of monoethanolamine in the presence of the catalysts of Examples 1–7 and Comparative Examples V1 and V2 was carried out as follows: a tubular reactor having a capacity of 100 ml, a length of 55 cm and an internal diameter of 1.5 cm was filled with 50 g of passivated catalyst and the latter was activated at 180° C. first with a mixture of 20% by volume of hydrogen/80% by volume of nitrogen and then with 100% by volume of hydrogen.

After the reaction temperature had been established at 175–195° C., depending on the activity of the catalyst, the reactor was charged with 10–30 g/h of monoethanolamine, 20–70 g/h of ammonia and 3–10 l (S.T.P.)/h of hydrogen. The conversion and the selectivity with respect to the components of ethylene diamine (EDA), aminoethylethanolamine (AEEA), diethylenetriamine (DETA) and piperazine were determined by gas chromatographic analysis of the discharged mixture. The catalyst space velocity is stated in relation to monoethanolamine (MEA). The results are summarized in Table 1 below.

TABLE 1

| Catalyst [No.] | Carrier | Pressure [bar] | Temperature [° C.] | MEA space velocity [kg/l · h] | $NH_3MEA$ [mol/mol] | Conversion [%] | EDA [%] | AEEA [%] | Piperazine [%] | DETA [%] |
|---|---|---|---|---|---|---|---|---|---|---|
| Comp. Expl. V1 | $Al_2O_3$ | 200 | 175 | 0.45 | 8 | 33.3 | 55.60 | 20.7 | 4.90 | 12.6 |
| Comp. | $Al_2O_3$ | 200 | 170 | 0.45 | 8 | 32.2 | 62.5 | 17.9 | 2.6 | 5.7 |
| Expl. V2 | | 200 | 185 | 0.45 | 8 | 46.4 | 61.8 | 15.0 | 5.0 | 7.4 |
| 1 | $Al_2O_3$ | 200 | 190 | 0.45 | 8 | 34.5 | 65.8 | 13.3 | 5.5 | 9.8 |
| | | | 195 | 0.45 | 8 | 46.2 | 65.2 | 10.7 | 7.7 | 10.7 |
| | | | 195 | 0.45 | 8 | 49.9 | 65.8 | 9.7 | 7.5 | 10.6 |
| 2 | $Al_2O_3$ | 200 | 195 | 0.45 | 8 | 33.6 | 73.0 | 11.9 | 6.0 | 7.0 |
| 3 | $Al_2O_3$ | 200 | 195 | 0.45 | 8 | 29.4 | 71.7 | 13.7 | 6.1 | 5.5 |
| 4 | $Al_2O_3$ | 200 | 195 | 0.45 | 8 | 50.1 | 69.5 | 8.2 | 8.0 | 9.8 |
| | | | 195 | 0.45 | 8 | 55.0 | 68.6 | 7.5 | 7.6 | 10.9 |
| 5 | $Al_2O_3$ | 200 | 185 | 0.45 | 8 | 50.6 | 70.3 | 8.0 | 6.4 | 12.1 |
| | | | 185 | 0.45 | 8 | 46.0 | 71.3 | 9.1 | 6.3 | 10.9 |
| 6 | $Al_2O_3$ | 200 | 185 | 0.45 | 8 | 46.2 | 70.3 | 7.9 | 6.1 | 13.5 |
| 7 | $Al_2O_3$ | 200 | 185 | 0.45 | 8 | 51.2 | 70.9 | 7.0 | 7.8 | 11.7 |

MEA = Monoethanolamine
AEEA = Aminoethylethanolamine
EDA = Ethylenediamine
DETA = Diethylenetriamine The results in Table 1 show that the selectivity in relation to ethylenediamine is substantially higher when the novel catalysts are used than when the known catalysts are used. Moreover, the stability of the novel catalysts is substantially higher than the stability of the comparative catalysts.

We claim:

1. A process for the preparation of an amination product by reacting an alkylene oxide, alcohol, aldehyde or ketone with ammonia or a primary or secondary amine in the presence of free hydrogen and in the presence of a catalyst composition comprising, based on the total weight of the catalyst, 0.1–6% by weight of cobalt, nickel or a mixture thereof, 0.001–25% by weight of ruthenium, 0–10% by weight of copper, and 0–5% by weight of promoters selected from the group consisting of iron, rhodium, palladium, platinum, iridium, osmium, silver, gold, chromium, molybdenum, tungsten, rhenium, zinc, cadmium, lead, manganese, tin, lithium, sodium, potassium, rubidium, cesium, phosphorus, arsenic, antimony, bismuth, tellurium, thallium, or mixtures thereof, on a porous metal oxide carrier, said carrier constituting the remainder by weight of the catalyst.

2. A process as claimed in claim 1, wherein an ethylene glycol or an ethanolamine is aminated with, or in the presence of, ammonia, an ethanolamine, an ethylenediamine or a diethylenetriamine.

3. A process as claimed in claim 1, which is carried out continuously.

* * * * *